(12) United States Patent
Nyquist

(10) Patent No.: US 11,134,845 B2
(45) Date of Patent: *Oct. 5, 2021

(54) LOCATION BASED PATIENT MONITORING

(71) Applicant: Cardiac Pacemakers, Inc., St. Paul, MN (US)

(72) Inventor: Benjamin J Nyquist, Mahtomedi, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/747,358

(22) Filed: Jan. 20, 2020

(65) Prior Publication Data

US 2020/0146552 A1   May 14, 2020

Related U.S. Application Data

(63) Continuation of application No. 16/055,562, filed on Aug. 6, 2018, now Pat. No. 10,588,510.

(60) Provisional application No. 62/543,910, filed on Aug. 10, 2017.

(51) Int. Cl.
| | |
|---|---|
| *A61B 5/00* | (2006.01) |
| *A61B 5/0205* | (2006.01) |
| *A61B 5/11* | (2006.01) |
| *A61N 1/372* | (2006.01) |
| *A61B 5/361* | (2021.01) |
| *A61B 5/363* | (2021.01) |
| *G16H 40/20* | (2018.01) |
| *A61N 1/36* | (2006.01) |

(52) U.S. Cl.
CPC .......... *A61B 5/0022* (2013.01); *A61B 5/0006* (2013.01); *A61B 5/0205* (2013.01); *A61B 5/1112* (2013.01); *A61N 1/37282* (2013.01); *A61B 5/0031* (2013.01); *A61B 5/1113* (2013.01); *A61B 5/361* (2021.01); *A61B 5/363* (2021.01); *A61B 2505/00* (2013.01); *A61B 2560/0209* (2013.01); *A61N 1/36014* (2013.01); *G16H 40/20* (2018.01)

(58) Field of Classification Search
CPC ...................................................... A61B 5/00
See application file for complete search history.

(56) References Cited

U.S. PATENT DOCUMENTS

| | | |
|---|---|---|
| 5,752,976 A | 5/1998 | Duffin et al. |
| 6,544,171 B2 | 4/2003 | Beetz et al. |
| 6,553,262 B1 | 4/2003 | Lang et al. |
| (Continued) | | |

FOREIGN PATENT DOCUMENTS

WO    WO-2019032435 A1    2/2019

OTHER PUBLICATIONS

"U.S. Appl. No. 16/055,562, Non Final Office Action dated Aug. 7, 2019", 14 pgs.

(Continued)

*Primary Examiner* — Nabil H Syed
*Assistant Examiner* — Cal J Eustaquio
(74) *Attorney, Agent, or Firm* — Schwegman Lundberg & Woessner, P.A.

(57) ABSTRACT

This document discusses, among other things, patient monitoring systems, apparatus, and methods that change the operation of an ambulatory medical device (AMD) using geographic location information.

20 Claims, 4 Drawing Sheets

(56) References Cited

U.S. PATENT DOCUMENTS

| | | |
|---|---|---|
| 6,677,858 B1 | 1/2004 | Faris et al. |
| 6,747,555 B2 | 6/2004 | Fellenstein et al. |
| 6,747,556 B2 | 6/2004 | Medema et al. |
| 6,937,150 B2 | 8/2005 | Medema et al. |
| 6,940,403 B2 | 9/2005 | Kail, IV |
| 6,982,639 B2 | 1/2006 | Brackett et al. |
| 7,001,334 B2 | 2/2006 | Reed et al. |
| 7,154,398 B2 | 12/2006 | Chen et al. |
| 7,289,786 B2 | 10/2007 | Krasner |
| 7,321,774 B1 | 1/2008 | Lau et al. |
| 7,676,268 B2 | 3/2010 | Hettrick et al. |
| 7,789,828 B2 | 9/2010 | Clapp |
| RE42,934 E | 11/2011 | Thompson et al. |
| 10,588,510 B2 | 3/2020 | Nyquist |
| 2004/0082840 A1* | 4/2004 | Chen ............ A61B 5/1112 600/300 |
| 2006/0235728 A1 | 10/2006 | Yogesh |
| 2007/0067005 A1* | 3/2007 | Schatz ............ A61N 1/37211 607/59 |
| 2008/0122616 A1 | 5/2008 | Warner |
| 2008/0228090 A1 | 9/2008 | Wariar et al. |
| 2009/0063187 A1 | 3/2009 | Johnson et al. |
| 2013/0024382 A1* | 1/2013 | Dala ............ G06F 21/577 705/51 |
| 2013/0245387 A1 | 9/2013 | Patel |
| 2013/0325508 A1* | 12/2013 | Johnson ............ G06F 19/3418 705/3 |
| 2014/0257070 A1* | 9/2014 | Blomqvist ............ A61B 5/7239 600/374 |
| 2014/0320307 A1 | 10/2014 | Matsuno et al. |
| 2015/0244687 A1* | 8/2015 | Perez ............ G06F 21/604 726/4 |
| 2016/0066843 A1 | 3/2016 | Mensinger et al. |
| 2016/0366557 A1 | 12/2016 | Gallegos et al. |
| 2017/0039504 A1* | 2/2017 | Ullman ............ G01S 19/13 |
| 2017/0087371 A1 | 3/2017 | Freeman et al. |
| 2017/0344716 A1* | 11/2017 | Abou-Sayed ............ G16H 40/20 |
| 2019/0046035 A1 | 2/2019 | Nyquist |

OTHER PUBLICATIONS

"U.S. Appl. No. 16/055,562, Notice of Allowance dated Nov. 8, 2019", 5 pgs.

"U.S. Appl. No. 16/055,562, Response filed Oct. 29, 2019 to Non Final Office Action dated Aug. 7, 2019", 10 pgs.

"International Application Serial No. PCT/US2018/045335, International Search Report dated Nov. 19, 2018", 4 pgs.

"International Application Serial No. PCT/US2018/045335, Written Opinion dated Nov. 19, 2018", 5 pgs.

"International Application Serial No. PCT/US2018/045335, International Preliminary Report on Patentability dated Feb. 20, 2020", 7 pgs.

\* cited by examiner

LOCATION BASED PATIENT MONITORING

CLAIM OF PRIORITY

This application is a continuation of U.S. application Ser. No. 16/055,562, filed Aug. 6, 2018, which claims the benefit of priority under 35 U.S.C. § 119(e) of U.S. Provisional Patent Application Ser. No. 62/543,910, filed on Aug. 10, 2017, each of which is herein incorporated by reference in its entirety.

TECHNICAL FIELD

This document relates generally to medical devices, and more particularly, but not by way of limitation, to systems, devices, and methods for monitoring patients using information corresponding to their location.

BACKGROUND

Heart failure (HF) can be described as a reduced ability of a heart to sufficiently deliver blood to meet bodily needs, affecting over five million people in the United States alone. HF is typically a chronic condition, but can also occur suddenly, affecting the left, right, or both sides of a heart. Common causes of HF include coronary artery disease, myocardial infarction, high blood pressure, atrial fibrillation, valvular heart disease, alcoholism, infection, cardiomyopathy, or one or more other conditions leading to a decreased pumping efficiency of the heart.

An arrhythmia is an abnormal heart rhythm, or any heart rhythm (e.g., fast, slow, irregular, etc.) that is not a normal heart rhythm. A bradycardia is a condition where the heart beats too slowly (e.g., below 60 beats per minute) to deliver sufficient blood supply to meet bodily needs. In contrast, a tachycardia is a condition where the heart (or a portion of a heart) beats too quickly to delivery sufficient blood supply to meet bodily needs. Other arrhythmias can include, for example, premature, extra, or skipped heart beats, heart defects, atrial or ventricular fibrillation affecting one or more chambers of the heart.

An ambulatory medical devices (AMD), such as an implantable, wearable, or other external medical device, can be configured to monitor, detect, or treat various conditions, such as arrhythmias, HF, or any other condition that a patient might have.

SUMMARY

This document discusses, among other things, patient monitoring systems, apparatus, and methods that use information corresponding to the geographic location of patient. In some examples, the information corresponding to the geographic location of the patient may be used to transition an ambulatory medical device (AMD) from a first monitoring mode to a second monitoring mode. For example, the information corresponding to the geographic location of the patient may indicate that the patient is at a medical care facility and the state of the AMD may be modified accordingly. In this or other examples, a mobile monitor can be configured to determine the geographic location of the patient and may be configured to send that determined geographic location information to the AMD, and the AMD can be configured to transition from the first monitoring mode to the second monitoring mode using the determined geographic location. In other examples, other information, such as patient or user information, or scheduling information, can be used to transition the AMD from the first monitoring mode to the second monitoring mode.

Example 1 is a system comprising: a mobile monitor configured to determine a geographic location; and an ambulatory medical device (AMD), communicatively coupled to the mobile monitor, the AMD configured to detect physiologic information from the patient using a first monitoring mode and a second monitoring mode, wherein the AMD is configured to receive the determined geographic location from the mobile monitor; and wherein the AMD is configured to switch between the first monitoring mode and the second monitoring mode according to the determined geographic location.

In Example 2, the subject matter of Example 1 optionally includes wherein, in response to the determined geographic location indicating that the patient is at a medical care facility, the mobile monitor is configured to instruct the AMD to switch from the first monitoring mode to the second monitoring mode.

In Example 3, the subject matter of Example 2 optionally includes wherein the AMD is configured to switch from the second monitoring mode to a third monitoring mode, different than the first and second monitoring modes, in response to the determined geographic location indicating that the patient is no longer at the medical care facility.

In Example 4, the subject matter of any one or more of Examples 1-3 optionally include wherein the first monitoring mode is a pre-hospitalization mode and the second monitoring mode is an in-clinic mode, wherein the second monitoring mode consumes more power than the first monitoring mode.

In Example 5, the subject matter of any one or more of Examples 1-4 optionally include wherein the AMD is configured to switch from the first monitoring mode to the second monitoring mode in response to the determined geographic location indicating that the patient has been at a medical care facility for a period longer than a specified amount of time.

In Example 6, the subject matter of any one or more of Examples 1-5 optionally include wherein the mobile monitor is configured to receive user confirmation that the patient is seeking medical attention, and wherein the AMD is configured to transition from the first monitoring mode to the second monitoring mode in response to the determined geographic location indicating that the patient is at a medical care facility and the mobile monitor receiving user confirmation that the patient is seeking medical attention.

In Example 7, the subject matter of any one or more of Examples 1-6 optionally include wherein the mobile monitor includes a mobile electronic device configured to receive location information including at least one of global positioning system (GPS), radio frequency identification (RFID), Bluetooth®, Wi-Fi®, near-field communication (NFC), cellular network, or paging network location information.

In Example 8, the subject matter of any one or more of Examples 1-7 optionally include wherein the mobile monitor, in response to the determined geographic location, is configured to prompt a user to instruct the AMD to upload detected physiologic information to a storage location remote from the AMD.

Example 9 is a system comprising: an ambulatory medical device (AMD) configured to detect physiologic information from a patient and to receive information corresponding to a geographic location of the patient, wherein the AMD is configured to transition from a first monitoring mode to a second monitoring mode in response to the received information corresponding to the geographic location of the patient indicating that the patient is at a medical care facility.

In Example 10, the subject matter of Example 9 optionally includes wherein the AMD, in the first monitoring mode, is configured to detect or transmit physiologic information from the patient in an ambulatory, pre-hospitalization mode, and wherein the AMD, in the second monitoring mode, is configured to detect or transmit physiologic information from the patient in an in-clinic mode that consumes more power than the ambulatory mode.

Example 11 is a system comprising: a mobile monitor including scheduling information of a patient; an ambulatory medical device (AMD), communicatively coupled to the mobile monitor, the AMD configured to detect physiologic information from the patient, wherein the AMD is configured to transition from a first monitoring mode to a second monitoring mode in response to the scheduling information including a scheduled appointment for the patient at a medical care facility.

In Example 12, the subject matter of Example 11 optionally includes wherein the mobile monitor is configured to determine a geographic location, and wherein the AMD is configured to transition from the first monitoring mode to the second monitoring mode in response to the scheduled appointment for the patient at the medical care facility and the determined geographic location indicating that the patient is at or near the medical care facility.

Example 13 is a system comprising: an ambulatory medical device (AMD) configured to detect physiologic information from a patient and to receive an indication of a scheduled appointment at a medical care facility for the patient; wherein the AMD is configured to upload physiologic information of the patient to a storage location remote from the AMD in response to the scheduled appointment at the medical care facility.

Example 14 is a system comprising: an ambulatory medical device (AMD) configured to detect physiologic information from a patient and to receive information corresponding to a geographic location of the patient; and wherein the AMD is configured to upload physiologic information of the patient to a storage location remote from the AMD in response to the geographic location of the patient indicating that the patient is at a medical care facility.

Example 15 is a system comprising: a mobile monitor configured to determine a geographic location; and an ambulatory medical device (AMD), communicatively coupled to the mobile monitor, the AMD configured to detect physiologic information from a patient, wherein the mobile monitor is configured to prompt a user to upload physiologic information of the patient to a storage location remote from the AMD in response to the geographic location indicating that the patient is at a medical care facility.

Example 16 is a system comprising: a mobile monitor configured to determine a geographic location; and an ambulatory medical device (AMD), communicatively coupled to the mobile monitor, the AMD configured to detect physiologic information from the patient using a first monitoring mode and a second monitoring mode, wherein the AMD is configured to receive the determined geographic location from the mobile monitor; and wherein the AMD is configured to switch between the first monitoring mode and the second monitoring mode according to the determined geographic location.

In Example 17, the subject matter of Example 16 optionally includes wherein, in response to the determined geographic location indicating that the patient is at a medical care facility, the mobile monitor is configured to instruct the AMD to switch from the first monitoring mode to the second monitoring mode.

In Example 18, the subject matter of Example 17 optionally includes wherein the AMD is configured to switch from the first monitoring mode to the second monitoring mode in response to the determined geographic location indicating that the patient has been at a medical care facility for a period longer than a specified amount of time.

In Example 19, the subject matter of any one or more of Examples 16-18 optionally include wherein the second monitoring mode consumes more power than the first monitoring mode.

In Example 20, the subject matter of any one or more of Examples 16-19 optionally include wherein the first monitoring mode is a pre-hospitalization mode and the second monitoring mode is an in-clinic mode.

In Example 21, the subject matter of any one or more of Examples 16-20 optionally include wherein the AMD is configured to switch from the second monitoring mode to a third monitoring mode, different than the first and second monitoring modes, in response to the determined geographic location indicating that the patient is no longer at the medical care facility.

In Example 22, the subject matter of any one or more of Examples 16-21 optionally include wherein the mobile monitor is configured to receive user confirmation that the patient is seeking medical attention, and wherein the AMD is configured to transition from the first monitoring mode to the second monitoring mode in response to the determined geographic location indicating that the patient is at a medical care facility and the mobile monitor receiving user confirmation that the patient is seeking medical attention.

In Example 23, the subject matter of any one or more of Examples 16-22 optionally include wherein the AMD includes a risk circuit configured to determine a risk of a worsening medical condition using the detected physiologic information, wherein the risk circuit, in the first monitoring mode, is configured to determine the risk using a first weighting of detected physiologic information or a comparison of the detected physiologic information to a first threshold, and wherein the risk circuit, in the second monitoring mode, is configured to determine the risk using a second weighting of detected physiologic information or a comparison of the detected physiologic information to a second threshold, the second threshold different than the first threshold.

In Example 24, the subject matter of any one or more of Examples 16-23 optionally include wherein the mobile monitor includes a mobile electronic device configured to receive location information including at least one of global positioning system (GPS), radio frequency identification (RFID), Bluetooth®, Wi-Fi®, near-field communication (NFC), cellular network, or paging network location information.

In Example 25, the subject matter of any one or more of Examples 16-24 optionally include wherein the mobile monitor, in response to the determined geographic location, is configured to prompt a user to instruct the AMD to upload detected physiologic information to a storage location remote from the AMD.

Example 26 is a system comprising: an ambulatory medical device (AMD) configured to detect physiologic information from a patient and to receive information corresponding to a geographic location of the patient, wherein the AMD is configured to transition from a first monitoring mode to a second monitoring mode in response to the received information corresponding to the geographic location of the patient indicating that the patient is at a medical care facility.

In Example 27, the subject matter of Example 26 optionally includes wherein the AMD, in the first monitoring mode, is configured to detect or transmit physiologic information from the patient in an ambulatory, pre-hospitalization mode, and wherein the AMD, in the second monitoring mode, is configured to detect or transmit physiologic information from the patient in an in-clinic mode that consumes more power than the ambulatory mode.

In Example 28, the subject matter of any one or more of Examples 26-27 optionally include wherein the AMD is configured to transition from the first monitoring mode to the second monitoring mode in response to the received information corresponding to the geographic location of the patient indicating that the patient has been at the medical care facility longer than a specified amount of time.

In Example 29, the subject matter of any one or more of Examples 26-28 optionally include wherein the AMD is configured to transition from the second monitoring mode to a third monitoring mode, different from the first and second monitoring modes, in response to the received information corresponding to the geographic location of the patient indicating that the patient is no longer at the medical care facility.

In Example 30, the subject matter of any one or more of Examples 26-29 optionally include wherein the AMD, in the first monitoring mode, is configured to detect physiologic information from the patient using a sensor at a first sensitivity or at a first frequency, and wherein the AMD, in the second monitoring mode, is configured to detect physiologic information from the patient using the sensor at a second sensitivity, more sensitive than the first sensitivity, or at a second frequency, higher than the first frequency.

In Example 31, the subject matter of any one or more of Examples 26-30 optionally include wherein the AMD, in the first monitoring mode, is configured to detect physiologic information from the patient using a first set of sensors, and wherein the AMD, in the second monitoring mode, is configured to detect physiologic information from the patient using a second set of sensors, different than the first set of sensors.

Example 32 is a method comprising: receiving information corresponding to a geographic location of a patient at an ambulatory medical device (AMD); detecting physiologic information from the patient using the AMD; and transitioning the AMD from an ambulatory data collection or transmission mode to an in-clinic data collection or transmission mode in response to the received information corresponding to the geographic location of the patient indicating that the patient is at a medical care facility.

In Example 33, the subject matter of Example 32 optionally includes wherein the in-clinic data collection or transmission mode has a higher power consumption than the ambulatory data collection or transmission mode.

In Example 34, the subject matter of any one or more of Examples 32-33 optionally include determining a geographic location of a mobile monitor; prompting, using the mobile monitor, user feedback in response to the received information corresponding to the geographic location of the patient indicating that the patient is at the medical care facility; and receiving, using the mobile monitor, user confirmation that the patient is seeking medical attention in response to the prompted user feedback, wherein the receiving information corresponding to the geographic location of the patient at the AMD includes receiving the determined location of the mobile monitor, and wherein the transitioning the AMD from the ambulatory data collection or transmission mode to the in-clinic data collection or transmission mode includes using the received user confirmation that the patient is seeking medical attention.

In Example 35, the subject matter of any one or more of Examples 32-34 optionally include wherein the transitioning the AMD from the ambulatory data collection or transmission mode to the in-clinic data collection or transmission mode includes in response to the received information corresponding to the geographic location of the patient indicating that the patient has been at the medical care facility for a specified amount of time.

In Example 36, the subject matter of any one or more of Examples 32-35 optionally include wherein the receiving information corresponding to the geographic location of the patient at the ambulatory medical device (AMD) includes receiving at least one of global positioning system (GPS), radio frequency identification (RFID), Bluetooth®, Wi-Fi®, near-field communication (NFC), cellular network, or paging network location information.

Example 37 is a system comprising: a mobile monitor including scheduling information of a patient; an ambulatory medical device (AMD), communicatively coupled to the mobile monitor, the AMD configured to detect physiologic information from the patient, wherein the AMD is configured to transition from a first monitoring mode to a second monitoring mode in response to the scheduling information including a scheduled appointment for the patient at a medical care facility.

In Example 38, the subject matter of Example 37 optionally includes wherein the AMD is configured to transition from the first monitoring mode to the second monitoring mode prior to the scheduled appointment.

In Example 39, the subject matter of any one or more of Examples 37-38 optionally include wherein the mobile monitor is configured to determine a geographic location, and wherein the AMD is configured to transition from the first monitoring mode to the second monitoring mode in response to the scheduled appointment for the patient at the medical care facility and the determined geographic location indicating that the patient is at or near the medical care facility.

Example 40 is a system comprising: an ambulatory medical device (AMD) configured to detect physiologic information from a patient and to receive an indication of a scheduled appointment at a medical care facility for the patient; wherein the AMD is configured to upload physiologic information of the patient to a storage location remote from the AMD in response to the scheduled appointment at the medical care facility.

In Example 41, the subject matter of Example 40 optionally includes wherein the AMD is configured to upload the physiologic information of the patient to the storage location prior to the scheduled appointment.

In Example 42, the subject matter of any one or more of Examples 40-41 optionally include wherein the AMD is configured to receive information corresponding to a geographic location of the patient, and wherein the AMD is configured upload physiologic information of the patient to the storage location remote from the AMD in response to the scheduled appointment at the medical care facility and the received information corresponding to the geographic location of the patient geographic location indicating that the patient is at or near the medical care facility.

Example 43 is a system comprising: an ambulatory medical device (AMD) configured to detect physiologic information from a patient and to receive information corresponding to a geographic location of the patient; and wherein the AMD is configured to upload physiologic information of the patient to a storage location remote from the AMD in response to the geographic location of the patient indicating that the patient is at a medical care facility.

Example 44 is a system comprising: a mobile monitor configured to determine a geographic location; and an ambulatory medical device (AMD), communicatively coupled to the mobile monitor, the AMD configured to detect physiologic information from a patient, wherein the mobile monitor is configured to prompt a user to upload physiologic information of the patient to a storage location remote from the AMD in response to the geographic location indicating that the patient is at a medical care facility.

Example 45 of subject matter (e.g., a system or apparatus) may optionally combine any portion or combination of any portion of any one or more of Examples 1-44 to include "means for" performing any portion of any one or more of the functions or methods of Examples 1-44, or a "non-transitory machine-readable medium" including instructions that, when performed by a machine, cause the machine to perform any portion of any one or more of the functions or methods of Examples 1-44.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
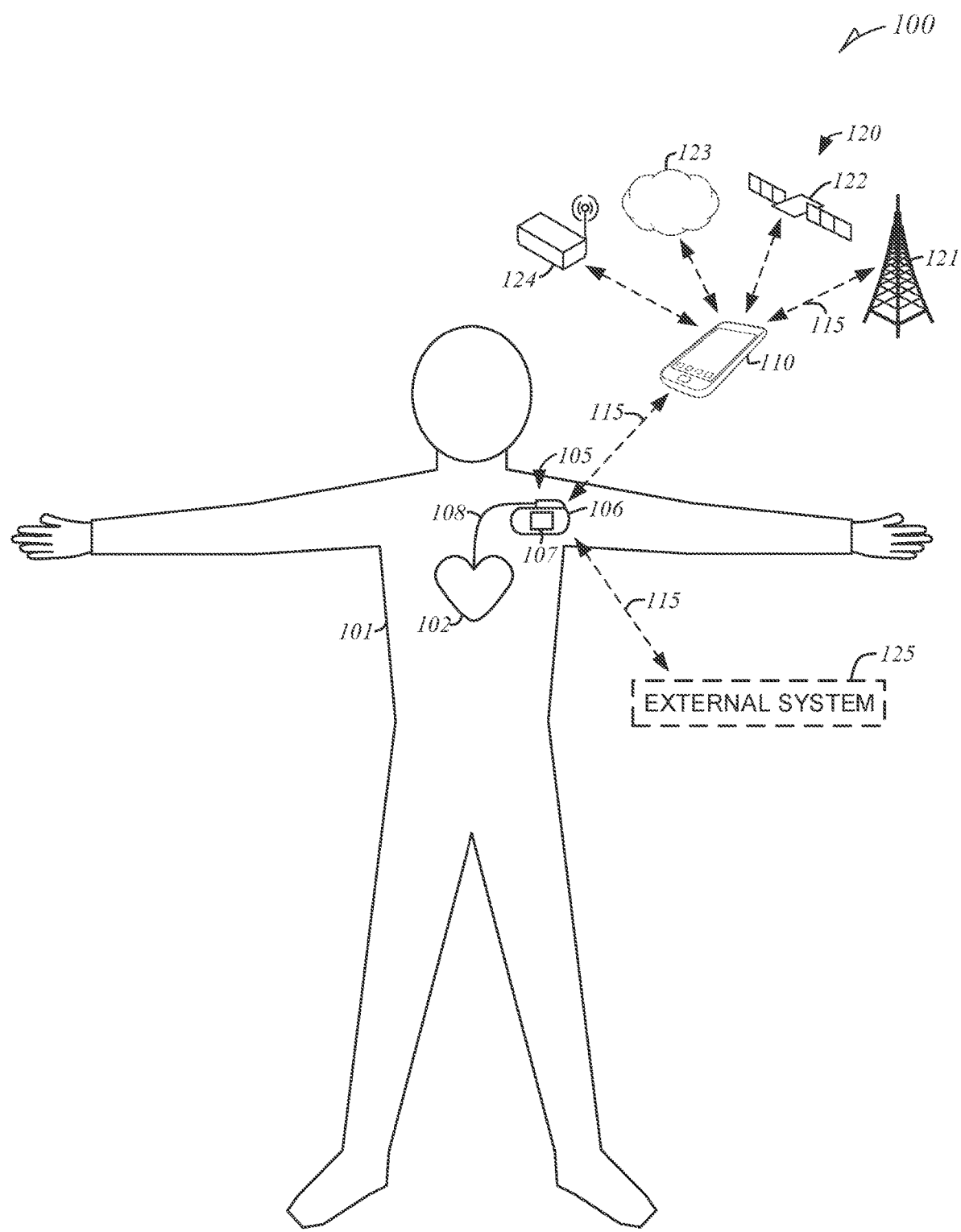
FIG. 1 illustrates an example patient management system including an ambulatory medical device (AMD) configured to detect physiologic information from a patient.

Patient management systems can include medical device(s) that can monitor one or more physiologic conditions of a patient and, as further described below, can use information corresponding to the location of the patient to adjust the operation of the medical device. For example, the medical device can use the information corresponding to the geographic information to adjust a monitoring of the patient, to adjust therapy delivered by the medical device to the patient, to adjust when data is transmitted to an external device or a server from the medical device, to provide a notification or alert, and/or other adjustments to the operation of the medical device.

In some examples, the patient management system can include a mobile monitor (e.g., a cellular phone, smart watch, tablet device, or one or more other mobile electronic device, etc.) configured to communicate with the medical device to monitor the one or more physiological conditions of the patient. The mobile monitor may be configured to periodically interrogate the medical device to send information to the medical or receive information from the medical device. In some cases, the mobile monitor may be configured to determine the geographic location of the patient and send information corresponding to the geographical location to the medical device. In an example, the geographic location of the patient can be determined or inferred using location information of the medical device or the mobile monitor. In certain examples, upon determining certain geographical locations of the patient (e.g. at medical care facility), the mobile monitor can provide information to a patient (e.g., notifications, prompts, etc.), and can receive patient or user feedback, including location information, confirmation of patient information, or other information, to, in some instances, confirm the location or condition of the patient. For example, the mobile monitor may prompt a user to provide feedback or information from the user, such as user identification, location information, whether the patient is seeking medical attention, one or more instructions for the mobile monitor or the medical device, such as to upload detected physiologic information to a storage area remote from the medical device, and/or whether to notify the patients physician of a medical condition. In an example, the medical device may automatically upload patient physiologic information to an external system when the patient enters a medical care facility, or alert a medical caregiver that the patient is seeking medical treatment from a medical care facility.

In some examples, the medical device or the mobile monitor may determine when the patient is no longer at the medical care facility, using information corresponding to a geographic location of the patient and/or other user information (e.g., patient or user confirmation such as patient response to prompts from the mobile monitor, etc.). In certain examples, admission or discharge information for the patient can be received (e.g., from the patient, from a user, from medical information, etc.) or separately inferred if the patient has been at or away from a medical care facility for a specified amount of time (e.g., more than 12 hours, days, etc.), some combination of both, etc. The medical device can alter or change operation using the geographic location information or other information corresponding to the geographic location of the patient.

FIG. 1 illustrates an example patient management system 100 including a medical device, such as an ambulatory medical device (AMD) 105 configured to detect physiologic information from a patient 101. In an example, the AMD 105 can be configured to transition from a first monitoring mode to a second monitoring mode in response to received information corresponding to a geographic location of the patient 101, the AMD 105, or one or more other devices in communication with the AMD 105, such as a mobile monitor 110 or one or more component of an external system 125. In other examples, the AMD 105 can be configured to transition from the first monitoring mode to the second monitoring mode in response to an instruction received from the patient 101, a clinician or other user, or one or more other devices, such as the mobile monitor 105 or an external system 125. In other examples, the AMD 105 can be configured to transition from the first monitoring mode to the second monitoring mode in response to scheduling or calendar information, such as an indication of a scheduled appointment for the patient 101 at a medical care facility.

The system 100 can perform a range of activities, including patient monitoring, diagnosis of a disease condition, or providing one or more therapies or other interventions. Such activities can be performed proximal to a patient 101, such as in a patient home, office, or medical care facility, or remote from the patient 101, such as through an external system 125, a mobile monitor 110, or through one or more other secure communication link 115 to or from the AMD 105.

As shown in FIG. 1, the AMD 105 is an implantable medical device (IMD), however, AMD 105 may be a wearable medical device, or one or more other implantable, leadless, subcutaneous, external, adherent, or wearable medical device configured to monitor, sense, or detect physiologic information from, or provide one or more therapies to treat various cardiac conditions relating to an ability of a heart to sufficiently deliver blood to a body, such as abnormal heart rhythm (e.g., atrial fibrillation (AF), heart failure (HF), or one or more other cardiac or other medical conditions). In an example, the AMD 105 can include one or more cardiac rhythm management (CRM) devices, such as a pacemaker, defibrillator, cardiac resynchronization therapy device, or cardiac monitor, or other housing 106 implanted in a patient 101 coupled to a lead system 108 including one or more implanted, transvenous, extravascular, or subcutaneous leads or catheters to position one or more electrodes or other sensors in, on, or about a heart 102 of the patient 101, or one or more other position in a thorax, abdomen, or neck of the patient 101.

The AMD 105 can include a detector circuit 107 configured to detect an event or process physiologic information received from the patient 101. The AMD 105 can include, be coupled to, or configured to receive information from one or more physiologic sensors, such as an accelerometer, a pressure sensor, an electrode, or one or more other sensors or detectors configured to sense, receive, or detect physiologic information from the patient. In an example, physiologic information can include cardiac electrical or mechanical information from the patient 101. The detector circuit 107 can include one or more electronic circuits configured to process, filter, extract, or isolate information relating to the one or more physiologic sensors. In an example, the detector circuit 107 can include a risk circuit for determining the risk of a medical event, such as worsening heart failure, using one or more different physiologic information. In other examples, the medical event can include a specific cardiac arrhythmia, such as atrial or ventricular brady- or tachyarrhythmia (e.g., atrial fibrillation (AF), atrial flutter, atrial tachycardia, supraventricular tachycardia, ventricular tachycardia, or ventricular fibrillation, etc.). In other examples, the medical event can include a fluid status, an indication of decreased cardiac output, or a detected acute or chronic worsening of one or more medical conditions, such as heart failure (HF), edema, etc.

The AMD 105 can be configured as a therapeutic device configured to treat arrhythmia or one or more other heart conditions. The AMD 105 may additionally include a therapy unit that may generate and deliver one or more therapies. The therapy can be delivered to the patient 101 via the lead system 108 and associated electrodes, or using one or more other delivery mechanisms. The therapy can include anti-arrhythmic therapy to treat an arrhythmia or to treat or control one or more complications from arrhythmias, such as syncope, congestive heart failure (CHF), or stroke, among others. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the AMD 105 can include a drug delivery system, such as a drug infusion pump to deliver drugs to the patient for managing arrhythmias, complications from arrhythmias, or one or more other cardiac conditions.

In other examples, the AMD 105 can include one or more leadless cardiac pacemakers (LCP) or other small (e.g., smaller than traditional implantable CRM devices), self-contained devices configured to detect physiologic information from, or provide one or more therapies or stimulation to, the heart 102 without traditional lead or implantable CRM device complications (e.g., required incision and pocket, complications associated with lead placement, breakage, or migration, etc.). In some cases, multiple LCP devices can be implanted in or about the heart to detect physiologic information from, or to provide one or more therapies or stimulations to, one or more chambers of the heart. The multiple LCP devices can communicate between themselves, or one or more other implanted or external devices.

In other examples, the AMD 105 can include one or more wearable or external medical sensors or devices (e.g., automatic external defibrillators (AEDs), Holter monitors, patch-based devices, smart watches, smart accessories, wrist- or finger-worn medical devices, etc.) configured to detect or monitor physiologic information of the patient without required implant or an in-patient procedure for placement, battery replacement, or repair.

The patient management system 100 can include, among other things, a respiration sensor configured to receive respiration information (e.g., a respiration rate (RR), a respiration volume (tidal volume), etc.), a heart sound sensor configured to receive heart sound information, an impedance sensor configured to receive impedance information, a cardiac sensor configured to receive cardiac electrical information, and an activity sensor configured to receive information about a physical motion (e.g., activity, posture, etc.), a pressure sensor configured to receive pressure information, one or more other sensors configured to receive physiologic information of the patient 101, or combinations thereof.

In an example, the AMD 105 can include a number of different modes. For example, in a first monitoring mode, such as an ambulatory or prehospitalization mode, the AMD 105 can provide long-term, ambulatory detection or transmission of physiologic information from the patient 101 to the mobile monitor 110 or one or more component of the external system 125. In some cases, the first monitoring mode may be configured to optimize the usable battery life of an AMD 105. In a second monitoring mode, the AMD 105 can provide detection or transmission of physiologic information from the patient 101 to the mobile monitor 110 or one or more component of the external system 125 using more power than the first monitoring mode. For instance, the second monitoring mode can increase detection or transmission of physiologic information from the patient 101 (e.g., with a higher detection or transmission sensitivity, frequency, using more or different sensors, detecting or computing one or more different indications, notifications, etc.) in anticipation of or during evaluation or treatment of the patient 101 at a medical care facility. While the first monitoring mode can include a normal, ambulatory operational mode of the AMD 105 (e.g. chronic disease monitoring), the second operation mode can be configured to monitor the patient in a higher risk mode (e.g. at a higher sensitivity or specificity for disease detection) and/or to prepare information for use by a medical caregiver (e.g., a clinician or other medical care worker) in an in-clinic or medical treatment setting, including detecting more information, with different monitoring or diagnostics, with better resolution or sensitivity, and/or uploading information, in certain examples, more or different information, at a time different than the normal, ambulatory schedule (e.g., immediately, at first availability, etc.).

In an example, physiologic information, such as detected using one or more different sensors, can be combined into a composite index or trend. In certain examples, the sensors can include heart sounds, thoracic impedance (e.g., to measure fluid accumulation, such as pulmonary edema), respiration (e.g., respiratory rate trend or rapid shallow breathing), heart rate, activity, among others. Physiologic information can be detected by the AMD 105, and in certain examples, be communicated to the external system 125, for example, using a wireless patient monitoring system, such as the Boston Scientific LATITUDE™ Advanced Patient Management System configured to receive transmissions from an implantable medical device (IMD) and securely transmit patient data to the host computer for processing.

In certain examples, a stratifier can be used to determine a patient risk level, and a combination of primary and secondary sensors depending on the patient risk level to create the composite index. In an example, the stratifier can use a combination of heart sound, respiration, and activity information from the patient to determine the risk level. If the stratifier indicates a low risk of worsening heart failure, the composite index can be determined using the primary sensors. If the stratifier indicates a high risk of worsening heart failure, the composite index can be determined using the primary sensors and a combination of secondary sensors, depending on the determined risk level. In an example, if the composite index exceeds an alert threshold, an alert can be provided to a medical caregiver or the patient 101, such as using the AMD 105, the external device 125, or the mobile monitor 110. In other examples, the AMD 105 can transition modes using the composite index or the primary sensors.

In some examples, once the information has been uploaded in the second monitoring mode, if no other information is requested, and the patient 101 remains at the medical care facility (e.g., for a specified amount of time, indicative of admission, such as more than 12 hours, days, etc.), the AMD 105 can transition to a third monitoring mode, easing the burden on the AMD 105, raising thresholds, and reducing power consumption. However, in other examples, the AMD 105 can remain in the second monitoring mode while the patient 101 is at the medical care facility, or the AMD 105 can return to the first monitoring mode, depending on, for example, the type of AMD 105, the type of medical care facility or treatment, or one or more other desired conditions. In some cases, the second monitoring mode may monitor the patient for improvement since reaching the medical facility and may, in some instances, be used to help determine if the patient should be discharged from the medical facility. Once the patient 101 has left the medical care facility, the AMD 105 can transition to a fourth monitoring mode (e.g., to monitor patient progress or regress to or from a pre-clinic baseline, etc.) or back to the first monitoring mode. If switching back to the first monitoring mode, in some cases, it may be after a period of time (e.g., days, weeks or months, to allow the patient 101 to transition back to a pre-clinic baseline). In some cases, the fourth monitoring mode may monitor the patient 101 for a period of time to help reduce hospital readmissions.

The mobile monitor 110 can include a handheld, wearable, or other mobile electronic device configured to detect a geographical location, such as using one or more sensors or circuits, or to receive geographical location information from a location-based system 120 through a communication link 115, or from a user or one or more other sensors or devices external to the mobile monitor 110. The location-based system 120 can include one or more of a cellular tower 121, a satellite 122, a network 123, a short-range (e.g., less than 100 m) wireless interface 124, or one or more other communication systems, such as a paging, near-field communication (NFC), Wi-Fi®, Bluetooth®, radio frequency identification (RFID), or other communication system, etc.

For example, the mobile monitor 110 can include a cellular phone or other mobile electronic device including a sensor or circuit configured to receive GPS information or other location information from the from one or more satellites 122. In an example, satellite location information can be supplemented using accelerometer or other communication or wireless data, such as cellular, Wi-Fi®, Bluetooth®, near-field communication (NFC), radio frequency identification (RFID), etc. In other example, location information can be received or detected using communication or wireless information, such as from the location-based system 120, etc.

The mobile monitor 110 can receive information from, or provide information to, the AMD 105 using a communication link 115. The geographic location of the patient 101 can be inferred or determined using the geographic location of the mobile monitor 110. In an example, the user of the mobile monitor 110 can be confirmed using feedback from a user, or using one or more sensors or information from the communication link 115. In other examples, the AMD 105 can be configured to detect or determine a geographic location of the patient instead of, or in addition to, the mobile monitor 110. Further, in certain examples, the mobile monitor 110 can instruct the AMD 105 to transition between modes in response to a determined or received indication that the patient is at a medical care facility, or is seeking medical treatment from a medical care facility.

In other examples, the patient 101 can use the mobile monitor 110 to transition the AMD 105 from the first monitoring mode to the second monitoring mode, depending on, for example, a status of the patient, etc. In certain examples, the mobile monitor 110 can prompt the user to inquire about patient status, for example, if the AMD 105 detects an abnormal condition, on a semi-regular basis, etc.

The external system 125 can include hardware/software system external and remote from the patient, such as a medical device programmer, a remote server-based patient management system, or alternatively a system defined predominantly by medical device specific software. The external system 125 can manage the patient 101 through the AMD 105 connected to the external system 125 via a communication link 115. In other examples, the AMD 105 can be connected to the mobile monitor 110 (e.g., a handheld or wearable electronic device, etc.) via a communication link 115.

The external system 125 can send information to, or receive information from, the AMD 105 or the via the communication link 115. Examples of the information can include real-time or stored physiological data from the patient 101, diagnostic data, such as detection of cardiac arrhythmias or events of worsening heart failure, responses to therapies delivered to the patient 101, or device operational status of the AMD 105 or a wearable device (e.g., battery status, lead impedance, etc.). In an example, one or more sensor inputs, weightings, or thresholds can be changed depending on the mode of the AMD 105. The communication link 115 can be an inductive telemetry link, a capacitive telemetry link, or a radio-frequency (RF) telemetry link, or wireless telemetry based on, for example, "strong" Bluetooth® or IEEE 802.11 wireless fidelity "Wi-Fi" interfacing standards. Other configurations and combinations of patient data source interfacing are possible.

By way of example and not limitation, the external system 125 can include an external device in proximity of the AMD 105, and a remote device in a location relatively distant from the AMD 105 in communication with the external device via a telecommunication network. Examples of the external device can include a medical device programmer, etc.

The remote device can be configured to evaluate collected patient information and provide alert notifications, among other possible functions. In an example, the remote device can include a centralized server acting as a central hub for collected patient data storage and analysis. The server can be configured as a uni-, multi-, or distributed computing and processing system. The remote device can receive patient data from multiple patients including, for example, the patient 101. The patient data can be collected by the AMD 105, among other data acquisition sensors or devices associated with the patient 101. The server can include a memory device to store the patient data in a patient database. The server can include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the AMD 105. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device may additionally include one or more locally configured clients or remote clients securely connected over the network to the server. Examples of the clients can include personal desktops, notebook computers, mobile devices, or other computing devices. System users, such as medical caregivers (e.g., clinicians or other medical care workers), may use the clients to securely access stored patient data assembled in the database in the server, and to select and prioritize patients and alerts for health care provisioning. In addition to generating alert notifications, the remote device, including the server and the interconnected clients, may also execute a follow-up scheme by sending follow-up requests to the AMD 105, or by sending a message or other communication to the patient 101, clinician or authorized third party as a compliance notification.

The network can provide wired or wireless interconnectivity. In an example, the network can be based on the Transmission Control Protocol/Internet Protocol (TCP/IP) network communication specification, although other types or combinations of networking implementations are possible. Similarly, other network topologies and arrangements are possible.

One or more of the external device or the remote device can output the detected medical events to a system user, such as the patient or a medical caregiver, or to a process including, for example, an instance of a computer program executable in a microprocessor. In an example, the process can include an automated generation of recommendations for anti-arrhythmic therapy, or a recommendation for further diagnostic test or treatment. In an example, the external device or the remote device can include a respective display unit for displaying the physiological or functional signals, or alerts, alarms, emergency calls, or other forms of warnings to signal the detection of arrhythmias. In some examples, the external system 125 can include an external data processor configured to analyze the physiological or functional signals received by the AMD 105, and to confirm or reject the detection of arrhythmias. Computationally intensive algorithms, such as machine-learning algorithms, can be implemented in the external data processor to process the data retrospectively to detect cardia arrhythmias.

Portions of the AMD 105 or the external system 125 can be implemented using hardware, software, firmware, or combinations thereof. Portions of the AMD 105 or the external system 125 can be implemented using an application-specific circuit that can be constructed or configured to perform one or more functions, or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

Figure 2:
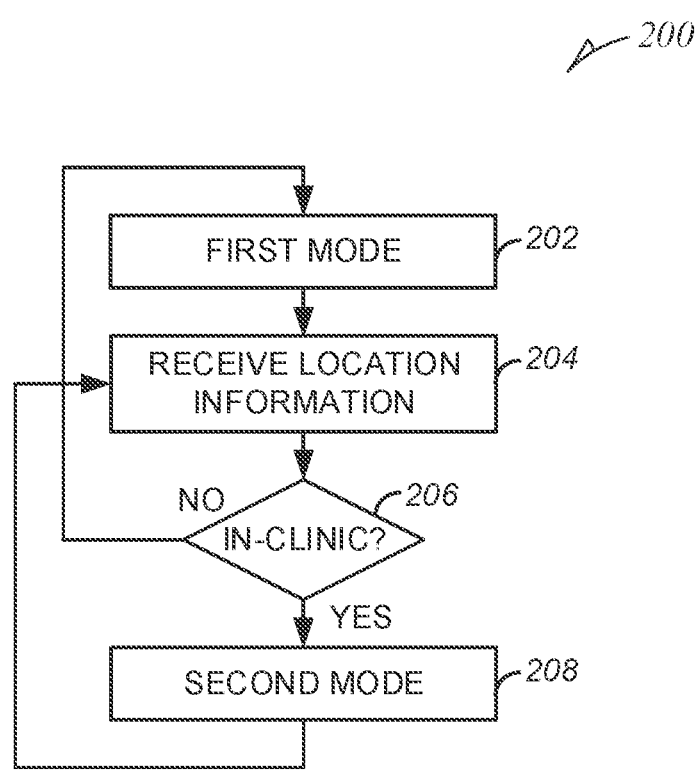
FIG. 2 illustrates a method of operating an ambulatory medical device (AMD) configured to detect physiologic information from a patient.

FIG. 2 illustrates a method 200 of operating an ambulatory medical device (AMD) configured to detect physiologic information from a patient. At 202, the AMD can operate in a first monitoring mode, such as an ambulatory or prehospitalization mode. At 204, the AMD can receive information corresponding to a geographic location of the patient. In an example, the AMD can receive geographic location information from a mobile monitor communicatively coupled to the AMD. In other examples, the AMD can receive geographic location information using on or more sensors or circuits of the AMD, or can receive information corresponding to the geographic location of the patient from the patient or one or more other users.

At 206, if the received information corresponding to the geographic location of the patient indicates that the patient is at a medical care facility (in certain examples, for a specified amount of time, such as 1 hour, 2 hours, 4 hours, 8 hours, 12 hours, 16 hours, 24 hours (e.g., greater than a typical commute past, delivery to, brief stop, work shift or visiting period), days, or one or more other time periods configured to reduce false positives for non-medical treatment events), at 208, the AMD can transition from the first monitoring mode to a second monitoring mode. The second monitoring mode can include an in-clinic monitoring mode, a monitoring mode that consumes more power than the first monitoring mode, or one or more other monitoring modes that monitors the patient at a higher resolution or with increased sensitivity or provides information to a medical caregiver in preparation for or during a time when the patient is located, scheduled, or otherwise indicated to receive medical treatment from a medical care facility (e.g., a scheduled appointment, etc.). In some examples, the first monitoring mode may monitor the patient for a worsening disease state and the second monitoring mode may monitor the patient for an improving disease state. In an example, the AMD can transition from the first monitoring mode to the second monitoring mode when the patient enters or is at the medical care facility, but, in some cases, delay one or more aspect of the second monitoring mode (e.g., upload of physiologic information, etc.) for a period of time (e.g., hours, days, etc.) to ensure the patient is seeking medical treatment.

If, at 206, the received information corresponding to the geographic location of the patient indicates that the patient is not at a medical care facility (in some cases, for the specified amount of time), process flow returns to 202, and the AMD remains in the first monitoring mode.

Figure 3:
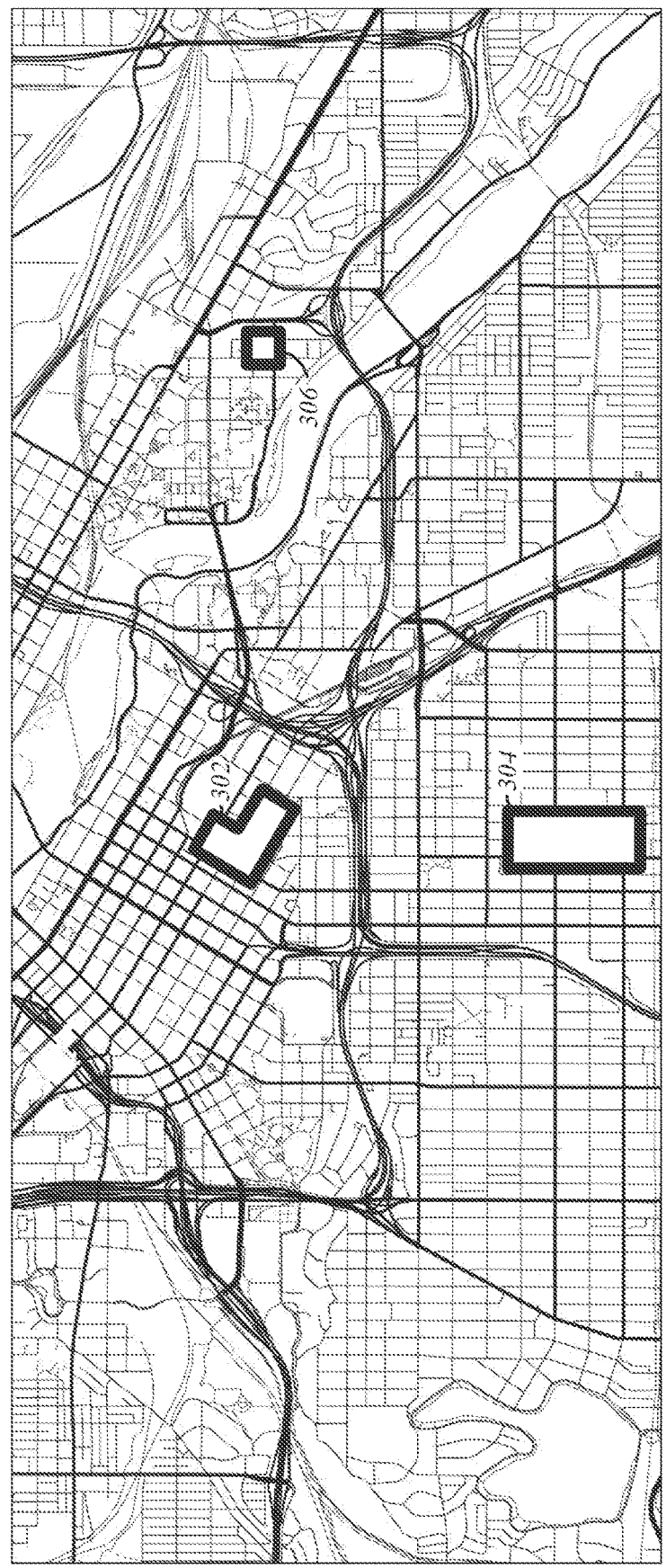
FIG. 3 illustrates an example interface including geographic locations of first, second, and third medical care facilities.

FIG. 3 illustrates an example interface 300 including geographic locations of first, second, and third medical care facilities 302, 304, 306. In an example, the location information of medical care facilities can be referenced to determine that the geographic location information of the mobile monitor, the AMD, or the patient is at a medical care facility.

The locations of medical care facilities can be input by a user or stored in a database to be accessed by the AMD, the mobile monitor, or an external system or one or more external system components. When the geographic location information (e.g., GPS, cellular data, etc.) indicates that the patient is at or approaching a known medical care facility, the AMD may transition from a first monitoring mode to one or more other monitoring modes. In an example, the medical care facilities can include emergency medical facilities. In other examples, the medical care facilities can include specific medical care facilities associated with regular, medical treatment of the patient. The medical care facilities can be tailored for specific patients, types of patients, patients having specific conditions, specific medical caregivers, etc. In other examples, if a patient's normal routine brings them close to or to a medical care facility, that medical care facility can be removed from the stored medical care facilities, or additional information can be required to transition the AMD from the first monitoring mode to the second monitoring mode, such as patient or user feedback or confirmation, RFID from inside the medical care facility, a Bluetooth® or Wi-Fi® connection to an internal medical care facility network or device, detection of a medical care facility pager network, or one or more other sensor readings indicating that the patient is inside the medical care facility, or has been admitted to or has entered a specific medical care facility, a specific location or part of the medical care facility, etc., where the second monitoring mode may be beneficial for the patient or to a medical caregiver.

In another example, the AMD can be configured to transition from the first monitoring mode to the second monitoring mode using scheduling information for the patient. The scheduling information can be indicative of a medical appointment at a medical care facility, and can be provided by the patient (e.g., input into or received by a mobile monitor or the AMD) or one or more other users, such as a medical caregiver. For example, the mobile monitor may be configured to access a calendar application on the mobile monitor and determine when the patient is scheduled for a medical visit. In an example, the AMD can receive scheduling information, or can receive an instruction from a mobile monitor or external system based on scheduling information. In certain examples, the scheduling information can be confirmed with patient or user feedback, or information corresponding to a geographic location of the patient (e.g., a geographic location of the mobile monitor or the AMD, etc.).

In some cases, the AMD may receive the scheduling information of the patient and may trigger the AMD to upload detected physiologic information to a storage area remote from the AMD, such as to the "cloud" or a remote server. In other instances, the mobile monitor may receive the scheduling information and may interrogate the AMD to receive the detected physiologic information stored on the AMD and then may transmit the detected physiologic information to the storage area remote from the AMD, such as to the "cloud" or a remote server. In either case, the geographic location of the patient may optionally be used to confirm that the patient is at the medical care facility prior to uploading the detected physiological data.

Figure 4:
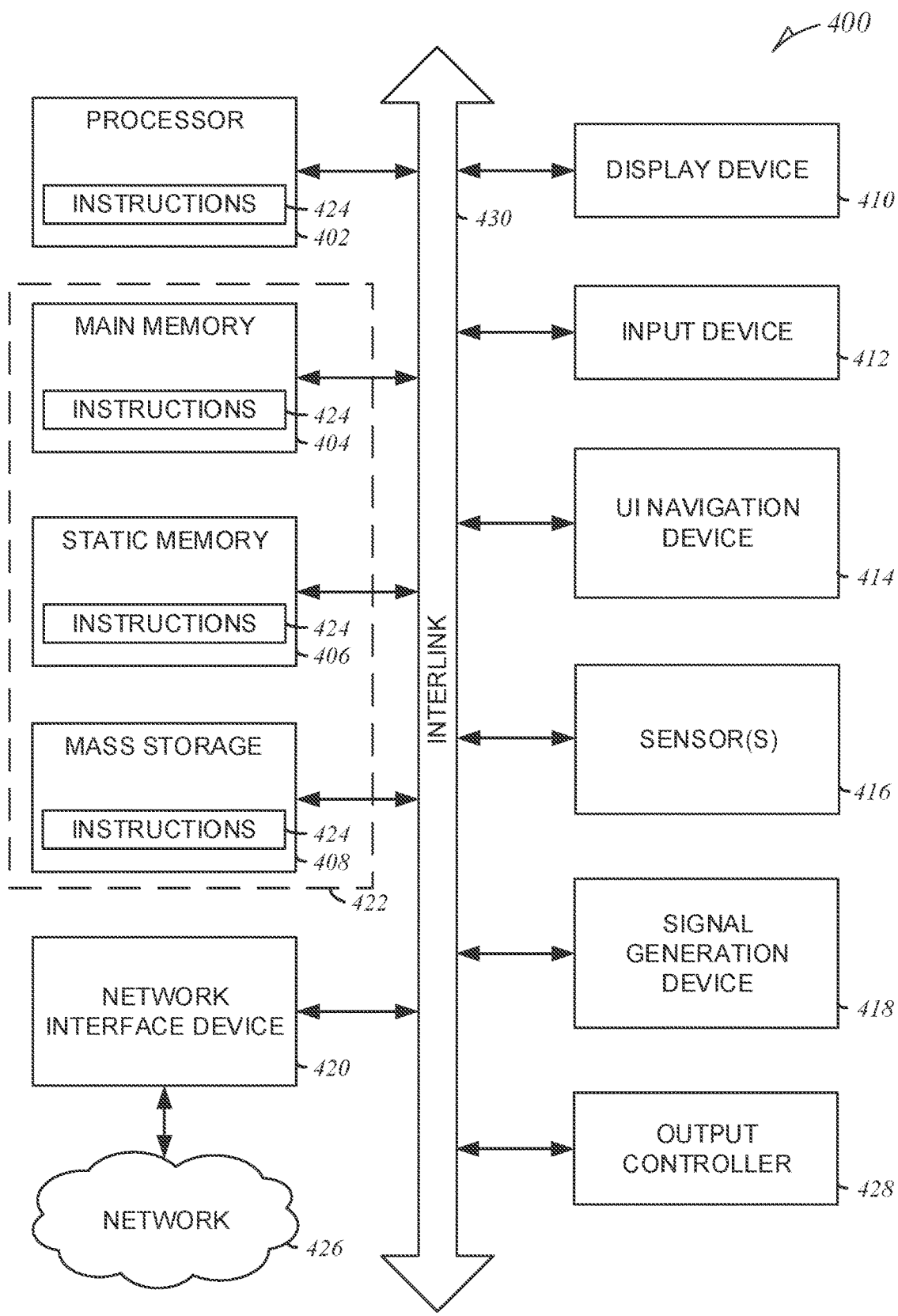
FIG. 4 illustrates a block diagram of an example machine upon which any one or more of the techniques discussed herein may perform.

FIG. 4 illustrates a block diagram of an example machine 400 upon which any one or more of the techniques (e.g., methodologies) discussed herein may perform. Portions of this description may apply to the computing framework of one or more of the medical devices described herein, such as the IMD, the external programmer, etc.

Examples, as described herein, can include, or may operate by, logic or a number of components, or mechanisms in the machine 400. Circuitry (e.g., processing circuitry) is a collection of circuits implemented in tangible entities of the machine 400 that include hardware (e.g., simple circuits, gates, logic, etc.). Circuitry membership can be flexible over time. Circuitries include members that may, alone or in combination, perform specified operations when operating. In an example, hardware of the circuitry can be immutably designed to carry out a specific operation (e.g., hardwired). In an example, the hardware of the circuitry can include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components can be used in more than one member of more than one circuitry. For example, under operation, execution units can be used in a first circuit of a first circuitry at one point in time and reused by a second circuit in the first circuitry, or by a third circuit in a second circuitry at a different time. Additional examples of these components with respect to the machine 400 follow.

In alternative embodiments, the machine 400 may operate as a standalone device or can be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 400 can include a hardware processor 402 (e.g., a central processing unit (CPU), a graphics processing unit (GPU), a hardware processor core, or any combination thereof), a main memory 404, a static memory (e.g., memory or storage for firmware, microcode, a basic-input-output (BIOS), unified extensible firmware interface (UEFI), etc.) 406, and mass storage 408 (e.g., hard drive, tape drive, flash storage, or other block devices) some or all of which may communicate with each other via an interlink (e.g., bus) 430. The machine 400 may further include a display unit 410, an alphanumeric input device 412 (e.g., a keyboard), and a user interface (UI) navigation device 414 (e.g., a mouse). In an example, the display unit 410, input device 412, and UI navigation device 414 can be a touch screen display. The machine 400 may additionally include a signal generation device 418 (e.g., a speaker), a network interface device 420, and one or more sensors 416, such as a global positioning system (GPS) sensor, compass, accelerometer, or other sensor. The machine 400 can include an output controller 428, such as a serial (e.g., universal serial bus (USB), parallel, or other wired or wireless (e.g., infrared (IR), near-field communication (NFC), etc.) connection to communicate or control one or more peripheral devices (e.g., a printer, card reader, etc.).

Registers of the processor 402, the main memory 404, the static memory 406, or the mass storage 408 may be, or include, a machine-readable medium 422 on which is stored one or more sets of data structures or instructions 424 (e.g., software) embodying or utilized by any one or more of the techniques or functions described herein. The instructions 424 may also reside, completely or at least partially, within any of registers of the processor 402, the main memory 404, the static memory 406, or the mass storage 408 during execution thereof by the machine 400. In an example, one or any combination of the hardware processor 402, the main memory 404, the static memory 406, or the mass storage 408 may constitute the machine-readable medium 422. While the machine-readable medium 422 is illustrated as a single medium, the term "machine-readable medium" can include a single medium or multiple media (e.g., a centralized or distributed database, and/or associated caches and servers) configured to store the one or more instructions 424.

The term "machine-readable medium" can include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine-readable medium examples can include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 can be further transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 420 can include one or more physical jacks (e.g., Ethernet, coaxial, or phone jacks) or one or more antennas to connect to the communications network 426. In an example, the network interface device 420 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 400, and includes digital or analog communications signals or other intangible medium to facilitate communication of such software. A transmission medium is a machine-readable medium.

While the foregoing description has been described with reference to heart failure and other cardiac diseases, it is contemplated that the devices and methods described could be used to monitor other diseases or in other implantable or external medical devices.

Various embodiments are illustrated in the figures above. One or more features from one or more of these embodiments can be combined to form other embodiments. Method examples described herein can be machine or computer-implemented at least in part. Some examples can include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
a mobile monitor configured to determine a geographic location; and
an ambulatory medical device (AMD), communicatively coupled to the mobile monitor, the AMD configured to detect physiologic information from a patient and to upload detected physiologic information from the AMD to a storage location remote from the AMD according to a normal upload schedule,
wherein the AMD is configured to receive the determined geographic location from the mobile monitor, and
wherein the AMD or the mobile monitor are configured to adjust the normal upload schedule of the AMD to an adjusted upload schedule responsive to the determined geographic location, wherein the normal upload schedule is different than the adjusted upload schedule.

2. The system of claim 1, wherein, in response to the determined geographic location indicating that the patient is at a medical care facility, the AMD is configured to upload detected physiologic information to the storage location immediately or at first availability, irrespective of the normal upload schedule.

3. The system of claim 1, wherein the AMD is configured to detect physiologic information from the patient using a first monitoring mode and a second monitoring mode,
wherein the AMD is configured to switch between the first monitoring mode and the second monitoring mode according to the determined geographic location,
wherein the first monitoring mode includes a first upload schedule and the second monitoring mode includes a second upload schedule different than the first upload schedule, and
wherein the first upload schedule is the normal upload schedule, and the second upload schedule is the adjusted normal upload schedule.

4. The system of claim 3, wherein, in response to the determined geographic location indicating that the patient is at a medical care facility, the mobile monitor is configured to instruct the AMD to switch from the first monitoring mode to the second monitoring mode.

5. The system of claim 4, wherein the AMD is configured to switch from the first monitoring mode to the second monitoring mode in response to the determined geographic location indicating that the patient has been at a medical care facility for a period longer than a specified amount of time.

6. The system of claim 3, wherein the second monitoring mode consumes more power than the first monitoring mode.

7. The system of claim 3, wherein the mobile monitor is configured to receive user confirmation that the patient is seeking medical attention, and
wherein the AMD is configured to transition from the first monitoring mode to the second monitoring mode in response to the determined geographic location indicating that the patient is at a medical care facility and the mobile monitor receiving user confirmation that the patient is seeking medical attention.

8. The system of claim 3, wherein the AMD includes a risk circuit configured to determine a risk of a worsening medical condition using the detected physiologic information,
wherein the risk circuit, in the first monitoring mode, is configured to determine the risk using a first weighting of detected physiologic information or a comparison of the detected physiologic information to a first threshold, and
wherein the risk circuit, in the second monitoring mode, is configured to determine the risk using a second weighting of detected physiologic information or a comparison of the detected physiologic information to a second threshold, the second threshold different than the first threshold.

9. The system of claim 1, wherein the mobile monitor includes at least one of a smart phone, a smart watch, a tablet device, or a mobile electronic device configured to receive location information including at least one of global positioning system (GPS), radio frequency identification (RFID), Bluetooth®, Wi-Fi®, near-field communication (NFC), cellular network, or paging network location information,
wherein the mobile monitor is separate from the AMD, and
wherein the storage location includes a cloud-based remote server separate from the mobile monitor and the AMD.

10. The system of claim 1, wherein the mobile monitor, in response to the determined geographic location, is configured to prompt a user to instruct the AMD to upload detected physiologic information to the storage location remote from the AMD.

11. A system comprising:
an ambulatory medical device (AMD) configured to detect physiologic information from a patient and to upload detected physiologic information from the AMD to a storage location remote from the AMD according to a normal upload schedule,
wherein the AMD is configured to receive information corresponding to a geographic location of the patient and to adjust the normal upload schedule of the AMD to an adjusted upload schedule responsive to the received information corresponding to the geographic location of the patient, wherein the normal upload schedule is different than the adjusted upload schedule.

12. The system of claim 11, wherein, in response to the received information corresponding to the geographic location of the patient indicating that the patient is at a medical care facility, the AMD is configured to upload detected physiologic information to the storage location immediately or at first availability, irrespective of the normal upload schedule.

13. The system of claim 11, wherein the AMD is configured to transition from a first monitoring mode to a second monitoring mode, and to adjust the normal upload schedule, in response to the received information corresponding to the geographic location of the patient indicating that the patient is at a medical care facility,
wherein the first monitoring mode includes a first upload schedule and the second monitoring mode includes a second upload schedule different than the first upload schedule, and
wherein the first upload schedule is the normal upload schedule, and the second upload schedule is the adjusted normal upload schedule.

14. The system of claim 13, wherein the AMD, in the first monitoring mode, is configured to detect or transmit physiologic information from the patient in an ambulatory, pre-hospitalization mode, and wherein the AMD, in the second monitoring mode, is configured to detect or transmit physiologic information from the patient in an in-clinic mode that consumes more power than the ambulatory mode.

15. The system of claim 13, wherein the AMD is configured to transition from the first monitoring mode to the second monitoring mode in response to the received information corresponding to the geographic location of the patient indicating that the patient has been at the medical care facility longer than a specified amount of time.

16. The system of claim 13, wherein the AMD, in the first monitoring mode, is configured to detect physiologic information from the patient using a sensor at a first sensitivity or at a first frequency, and
wherein the AMD, in the second monitoring mode, is configured to detect physiologic information from the patient using the sensor at a second sensitivity, more sensitive than the first sensitivity, or at a second frequency, higher than the first frequency.

17. The system of claim 13, wherein the AMD, in the first monitoring mode, is configured to detect physiologic information from the patient using a first set of sensors, and
wherein the AMD, in the second monitoring mode, is configured to detect physiologic information from the patient using a second set of sensors, different than the first set of sensors.

18. A method comprising:
receiving information corresponding to a geographic location of a patient at an ambulatory medical device (AMD);
detecting physiologic information from the patient using the AMD;
uploading detected physiologic information from the AMD to a storage location remote from the AMD according to a normal upload schedule; and
adjusting, using a mobile monitor or the AMD, the normal upload schedule of the AMD to an adjusted upload schedule responsive to the received information corresponding to the geographic location of the patient, wherein the normal upload schedule is different than the adjusted upload schedule.

19. The method of claim 18, comprising:
in response to the received information corresponding to the geographic location of the patient indicating that the patient is at a medical care facility, uploading, using the AMD, detected physiologic information to the storage location immediately or at first availability, irrespective of the normal upload schedule.

20. The method of claim 18, wherein detecting physiologic information from the patient using the AMD comprises using a first monitoring mode and a second monitoring mode, and
wherein the method comprises:
transitioning the AMD from the first monitoring mode to the second monitoring mode, in response to the received information corresponding to the geographic location of the patient indicating that the patient is at a medical care facility,
wherein the first monitoring mode includes a first upload schedule and the second monitoring mode includes a second upload schedule different than the first upload schedule, and
wherein the first upload schedule is the normal upload schedule, and the second upload schedule is the adjusted normal upload schedule.

* * * * *